United States Patent
Stehle et al.

(10) Patent No.: US 9,558,558 B2
(45) Date of Patent: Jan. 31, 2017

(54) INTERACTIVE FOLLOW-UP VISUALIZATION

(71) Applicant: KONINKLIJKE PHILIPS N.V., Eindhoven (NL)

(72) Inventors: Thomas Heiko Stehle, Eindhoven (NL); Astrid Ruth Franz, Eindhoven (NL); Carsten Meyer, Eindhoven (NL); Fabian Wenzel, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/779,358

(22) PCT Filed: Mar. 26, 2014

(86) PCT No.: PCT/IB2014/060153
§ 371 (c)(1),
(2) Date: Sep. 23, 2015

(87) PCT Pub. No.: WO2014/155299
PCT Pub. Date: Oct. 2, 2014

(65) Prior Publication Data
US 2016/0048965 A1 Feb. 18, 2016

Related U.S. Application Data

(60) Provisional application No. 61/806,046, filed on Mar. 28, 2013.

(51) Int. Cl.
G06K 9/00 (2006.01)
G06T 7/00 (2006.01)
(Continued)

(52) U.S. Cl.
CPC .......... *G06T 7/0044* (2013.01); *A61B 5/4064* (2013.01); *G06T 7/0016* (2013.01); *G06T 7/0081* (2013.01);
(Continued)

(58) Field of Classification Search
USPC ................................. 382/128–134
See application file for complete search history.

(56) References Cited

U.S. PATENT DOCUMENTS

| 2004/0240753 A1* | 12/2004 | Hu | G06T 7/608 |
| | | | 382/286 |
| 2005/0113680 A1* | 5/2005 | Ikeda | A61B 6/481 |
| | | | 600/425 |

(Continued)

FOREIGN PATENT DOCUMENTS

| WO | 2007144620 A2 | 12/2007 |
| WO | 2010023623 A1 | 3/2010 |
| WO | 2012138871 A2 | 10/2012 |

*Primary Examiner* — Alex Liew

(57) ABSTRACT

A system and method directed to receiving a first data set corresponding to patient data at a first time, receiving a second data set corresponding to patient data at a second time, segmenting a first region of interest in the first data set and a second region of interest in the second data set, the first and second regions corresponding to one another and aligning the first region of interest with the second region of interest to highlight a first contour indicating a change in size, shape and orientation between the first and second regions of interest.

20 Claims, 3 Drawing Sheets

(51) Int. Cl.
*A61B 5/00* (2006.01)
*G06T 7/60* (2006.01)

(52) U.S. Cl.
CPC ..... *G06T 7/602* (2013.01); *G06T 2207/10072* (2013.01); *G06T 2207/20104* (2013.01); *G06T 2207/20221* (2013.01); *G06T 2207/30016* (2013.01)

(56) References Cited

U.S. PATENT DOCUMENTS

| | | | |
|---|---|---|---|
| 2005/0215889 A1* | 9/2005 | Patterson, II | G06K 9/00 600/436 |
| 2006/0274061 A1* | 12/2006 | Wang | A61N 5/103 345/420 |
| 2007/0014453 A1* | 1/2007 | Nowinski | G06T 7/0028 382/128 |
| 2008/0021502 A1* | 1/2008 | Imielinska | A61B 6/032 607/1 |
| 2008/0097187 A1* | 4/2008 | Gielen | G06T 7/0012 600/409 |
| 2008/0123921 A1* | 5/2008 | Gielen | A61B 5/06 382/131 |
| 2008/0123922 A1* | 5/2008 | Gielen | A61B 5/06 382/131 |
| 2008/0123923 A1* | 5/2008 | Gielen | G06K 9/3216 382/131 |
| 2009/0252391 A1* | 10/2009 | Matsuda | A61B 5/055 382/131 |
| 2010/0091035 A1* | 4/2010 | Kirchberg | G06K 9/342 345/620 |
| 2011/0116702 A1* | 5/2011 | Bredno | G06T 7/608 382/131 |
| 2013/0230224 A1* | 9/2013 | Claude | A61B 5/055 382/131 |
| 2013/0251231 A1* | 9/2013 | Goto | A61B 5/055 382/131 |
| 2013/0289395 A1* | 10/2013 | Thiele | G06T 7/608 600/425 |
| 2016/0042524 A1* | 2/2016 | Wenzel | G06T 3/0093 382/128 |

* cited by examiner

INTERACTIVE FOLLOW-UP VISUALIZATION

CROSS-REFERENCE TO PRIOR APPLICATIONS

This application is the U.S. National Phase application under 35 U.S.C. §371 of International Application No. PCT/IB2014/060153, filed on Mar. 26, 2014, which claims the benefit of U.S. Patent Application No. 61/806,046, filed on Mar. 28, 2013. These applications are hereby incorporated by reference herein.

BACKGROUND

For many medical applications and examinations, it is useful to track the progress of tissue growth and/or shrinkage in the brain (e.g., to monitor brain atrophy in patients having neurodegenerative diseases, to determine a response of a cancerous tumor to treatment, etc.). To perform a diagnosis, a physician or other user typically compares the shape of the brain in a current brain scan to the shape from a previous brain scan. However, in many cases, the structural changes in the brain over time are subtle and therefore difficult to recognize. It therefore becomes cumbersome to properly assess an efficacy of a treatment or to track brain atrophy. There may be a need for an efficient process by which to streamline an analysis between different images.

SUMMARY

A system and method directed to receiving a first data set corresponding to patient data at a first time, receiving a second data set corresponding to patient data at a second time, segmenting a first region of interest in the first data set and a second region of interest in the second data set, the first and second regions corresponding to one another and aligning the first region of interest with the second region of interest to highlight a first contour indicating a change in size, shape and orientation between the first and second regions of interest.

BRIEF DESCRIPTION OF THE DRAWINGS

Several exemplary embodiments of the invention will be described in the following by way of example and with reference to the accompanying drawings in which.

DETAILED DESCRIPTION

The exemplary embodiments may be further understood with reference to the following description and appended drawings. The exemplary embodiments relate to an interactive visualization mode displaying structures in the brain captured via any imaging modality including, but not limited to, functional magnetic resonance imaging (fMRI), computed tomography (CT), Positron Emission Tomography (PET), magnetoencephalography (MEG) or any other imaging technique known in the art and with any therapy planning workstations including, but not limited to ViewForum, Pinnacle, FEW, etc. It is noted that although the exemplary embodiments are discussed with respect to imaging of the brain, the exemplary system and method may be applied to the imaging of any other anatomical region without deviating from the scope of this disclosure. The exemplary system and method provides a visualization mode wherein first and second images may be provided in an overlay with one another to aid in visualization of variations in structures therebetween. The first image may be captured at a baseline time period and recorded onto a storage medium along with details with respect to patient state, time of image capture, etc. The second image may be captured after any of a lapse of a predetermined time period, administration of a treatment, occurrence of a major medical event (e.g., stroke, etc.), or any other time period of interest and may be stored on a storage medium along with patient details. The exemplary system and method can perform a segmentation of structures of interest in each of the first and second images. The first and second images can then be registered in a single overlay and delineated such that any changes between corresponding segments can be highlighted on a display. The delineation may be displayed as an outline of the corresponding segments and may further indicate whether the change was an increase or decrease in an area of the brain over time (e.g., wherein an increase in area may be indicated by a solid line and a decrease may be indicated by a dotted line, wherein an increase in area may be indicated by a dotted line and a decrease may be indicated by a solid line, etc.). In some embodiments, the delineation may also display additional data including, but not limited to, area, circumference, volume, diameter (taken along one or both of a short and long axis), etc. of the highlighted portion. The exemplary system and method can enable a quick comparison of the structural differences between first and second images by providing an interactive visualization thereof. A user may toggle between each of the first, second and overlay images in turn to analyze any individual segments in greater detail and aid in making an analysis of a current state of the patient.

Figure 1:
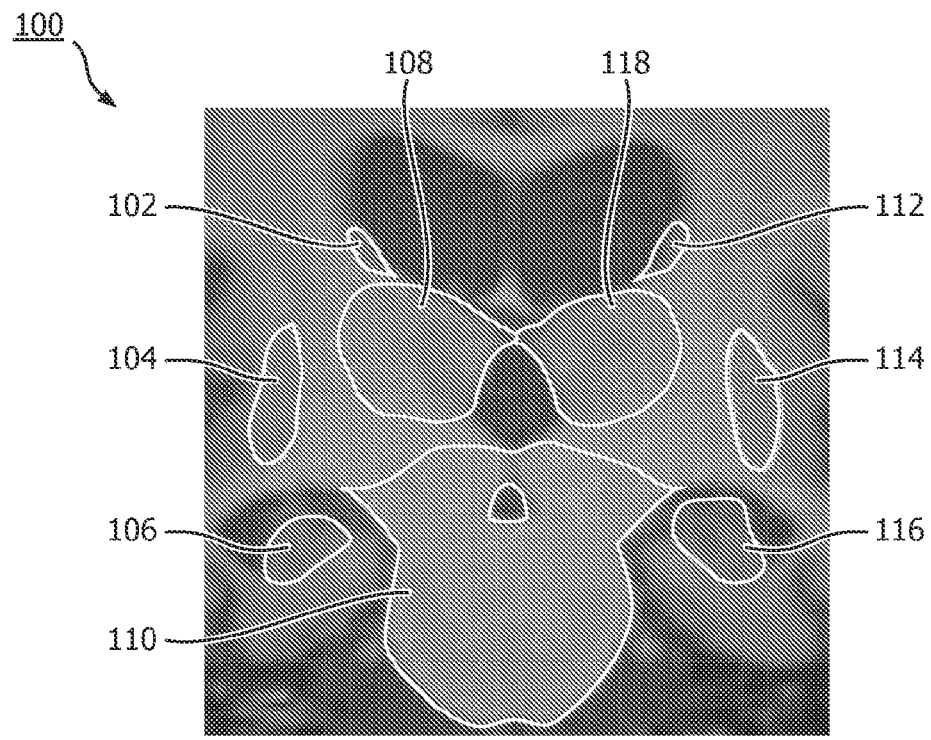
FIG. 1 depicts an overlay image according to a first exemplary embodiment.

In accordance with an exemplary method according to the invention, a first data set (not shown) can be captured and stored in any storage medium along with detailed information including, but not limited to, patient information, time and data of data capture and any additional user notes. A second data set 100, as shown in FIG. 1, can be captured after any of a lapse of a predetermined time period, administration of a treatment, occurrence of a major medical event (e.g., stroke, etc.), or any other time delay relative to capturing of the first data set. A brain segmentation tool can be used to segment multiple brain structures of interest 102-118 in each of the first data set (not shown) and the second data set 100, as those skilled in the art will understand. Each of the structures 102-118 may be marked by colored contours having different colors or, in another embodiment, different line styles (e.g., dashes, varying thicknesses, etc.). The first data set may be segmented at the time of capture or, in another embodiment, may be segmented when the second data set is captured.

Figure 2:
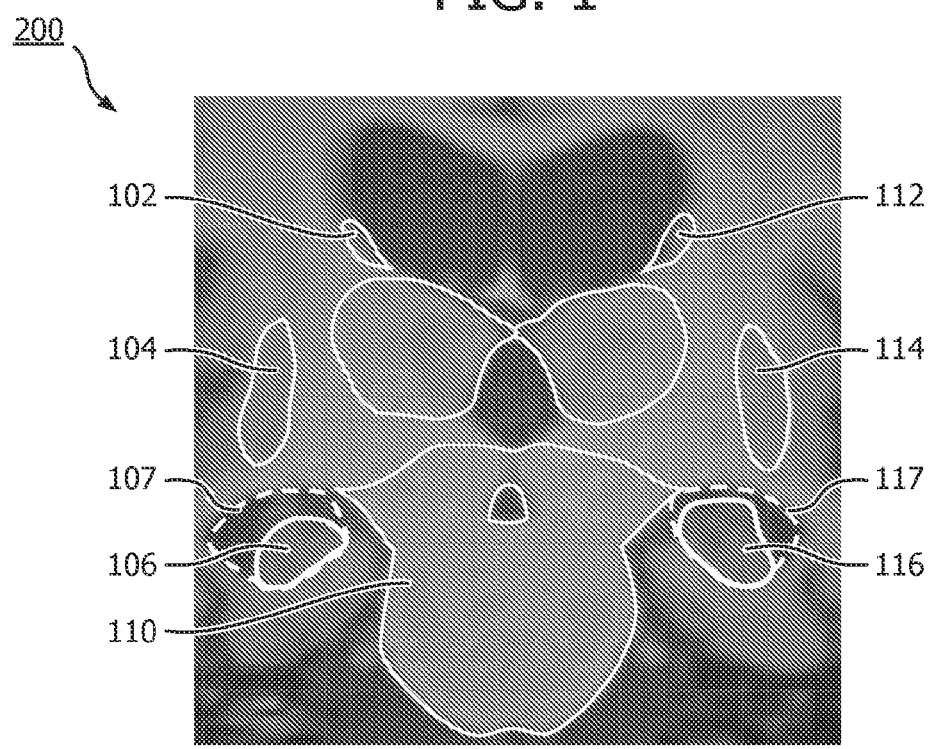
FIG. 2 depicts an overlay image according to a second exemplary embodiment.

FIG. 2 depicts an exemplary overlay image 200, which is a composite of first and second data sets corresponding to first and second brain scan images overlaid with one another. In an operative configuration, a user may select a comparison button to delineate all structural changes in the regions of interest 102-118 between the first and second data sets. Specifically, an exemplary procedure according to the invention is provided to overlay the first and second data sets in a manner such that corresponding structures 102-118 are aligned with one another, the procedure accounting for possible changes in anatomy between the first and second data sets. Specifically, a prerequisite for the visualization according to exemplary embodiments of the invention is the availability and co-registration of the structures 102-118 for each of the first and second data sets with either a rigid or deformable volume preserving constraint. This co-registration allows the segmented structures 102-118 of the first data set to appear at the correct position in the overlay image relative to their locations in the second data set. In the case of a bitmask-based segmentation, this can be achieved by co-registration of both the first and second data sets. The transformation between the first and second data sets is subsequently applied to the bitmask. In the case of a model-based segmentation, this may be achieved as described above with respect to the bitmask-based registration or, in another embodiment, by co-registration of meshes which represent the segmentation results. The resultant overlay image 200 displays delineated portions 107, 117 of the right and left hippocampus 106, 116, respectively. Specifically, the dashed line for the delineated portions 107, 117 are indicative of a size and shape of the right and left hippocampus as taken from the first data set (not shown). The solid lines of the right and left hippocampus 106, 116 are indicative of a current size and shape thereof, as taken from the second data set 200. In another exemplary embodiment, each of the left and right hippocampus 106, 116 and corresponding delineated portions 107, 117 may be marked with different contours including, but not limited to, different contour line colors, line thicknesses, line styles, etc. The image 200 provides a clear and easy to interpret visualization of any changes between the first and second data sets, thus eliminating a need for a user to toggle between multiple images to make a manual assertion of possible changes in any portion of the anatomy thereof.

Figure 3:
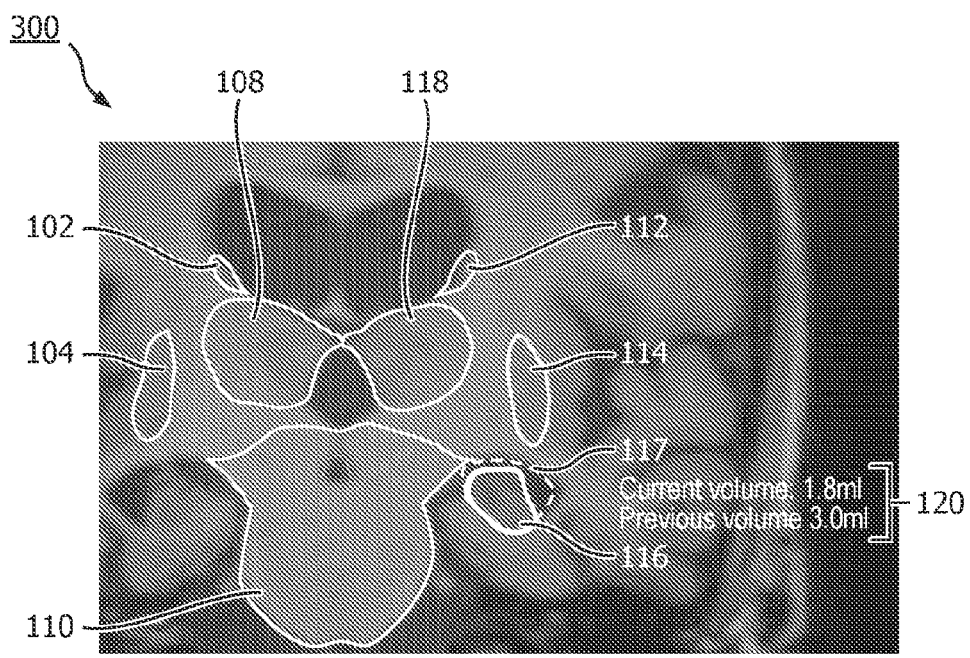
FIG. 3 depicts an overlay image according to a third exemplary embodiment.
Figure 4:
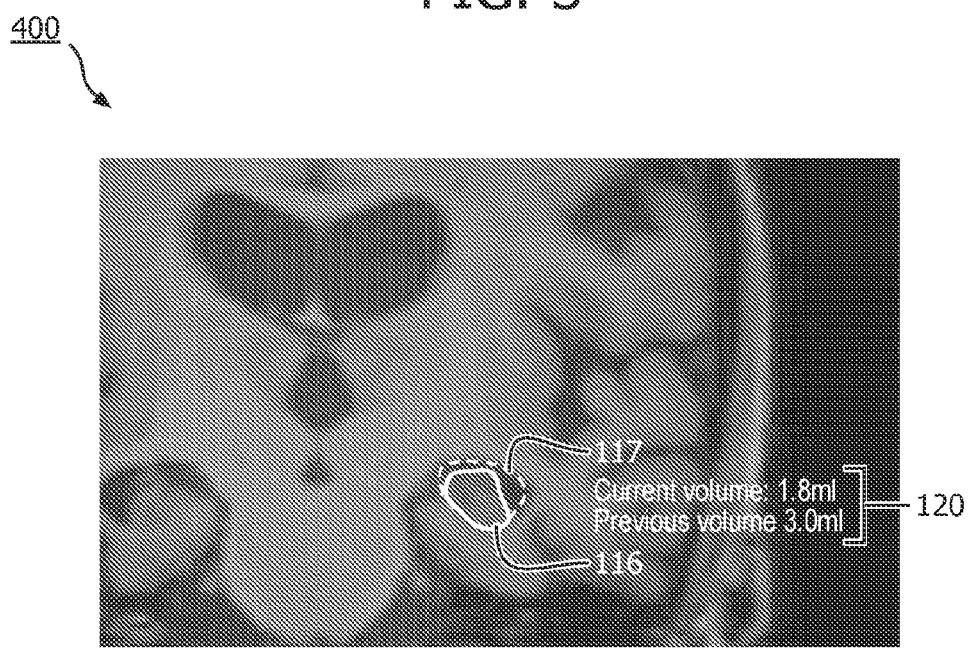
FIG. 4 depicts an overlay image according to a fourth exemplary embodiment.

FIG. 3 depicts an image 300 according to another exemplary embodiment of the invention. Specifically, a user may select any of the delineated portions 107, 117 by clicking on the corresponding structure on the image 200. In the present embodiment, a user may select either of the structure 116 which corresponds to a left hippocampus of the brain or the delineated portion 117 thereof. This selection prompts the display of quantitative information 120 corresponding to changes in the left hippocampus between the first and second data sets. The quantitative information 120 includes, but is not limited to, volume, area, circumference and diameter (taken alone one or both of the short and long axes) of the structure in the first and second data sets or the delineated portion of the overlay image 300. To improve clarity, the non-selected delineated portion 107 can be made invisible as long as the delineated portion 117 is being examined, as shown in FIG. 3. In another embodiment, as shown in FIG. 4, all non-selected structures 102-118 may also be made invisible so that only the selected delineated portion 117 is shown on an image 400. The quantitative information 120 may be displayed as a sticky overlay to the image 300, 400 such that a user may scroll through the image 300, 400 or first and second data sets thereof while the quantitative information 120 stays visible in place. In another embodiment, the quantitative information 120 may display data corresponding to only the first data set when the first data set (not shown) is viewed and display data corresponding to only the second data set 100 when the second data set 100 is viewed. The quantitative information 120 may be displayed in a color corresponding to a color of the corresponding structure. The system and method according to exemplary embodiments of the invention can allow a user to toggle between any of the first data set, second data set and overlay image 200, 300, 400 with a single click, thus enabling a user to easily analyze quantitative information relating thereto.

It is noted that although images 100, 200, 300, 400 are shown with particular structures, any combination of displayed information may be used without deviating from the scope of the invention. In one example, when selecting a structure 102-118 for analysis, only adjacently positioned structures are removed from the display while outlying structures which, for example, do not overlap the selected structure, remain visible. In another example, when displaying a structure, both the structure and its corresponding delineated portion are displayed as a 3D contour intersecting a 2D image slice. In yet another example, a button may be provided to trigger the display of volumetric information for some or all structures. In another example, any plurality or all of the structures of the overlaid image may be displayed in both states at once (i.e., from first and second data sets). In still another embodiment, first and second data sets may be displayed side-by-side with their respective segmentations. In yet another embodiment, an overlay image may be formed as an overlay of three or more images to, for example, track a progression of an abnormality between three or more sessions.

Figure 5:
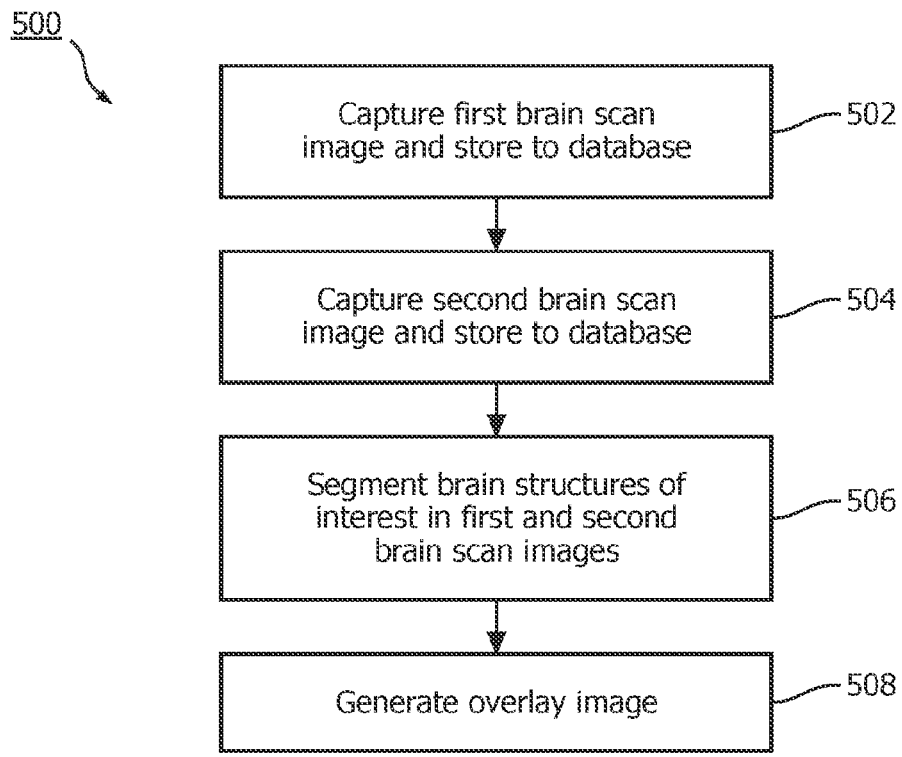
FIG. 5 depicts an exemplary method for generating an overlay.
Figure 6:
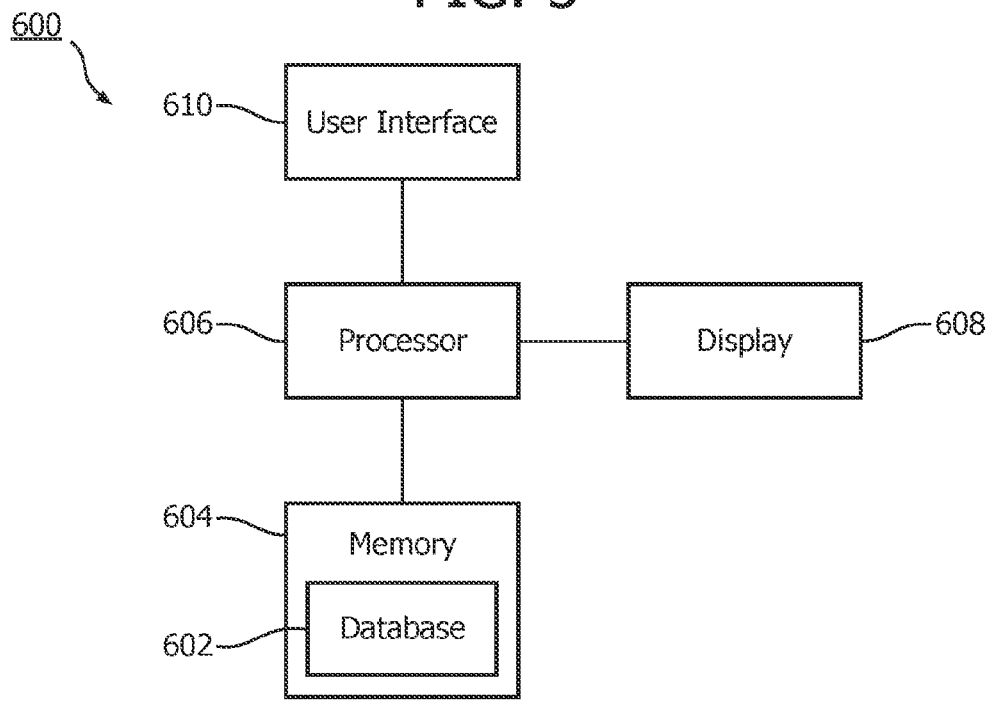
FIG. 6 shows a schematic drawing of a system according to an exemplary embodiment.

FIGS. 5-6 depict an exemplary method 500 and system 600 according to exemplary embodiments of the invention. In a first step 502, a first brain scan image (not shown) is captured and stored on a database 602 of a memory 604. In step 504, a second brain scan image 200 is captured and stored on the database 602. As those skilled in the art may appreciate, the capturing steps 502, 504 may be optionally omitted. Rather, a processor 606 may reference first and second brain scan images previously stored on the database 602. In step 506, the processor 606 segments one or more brain structures of interest in each of the first and second brain scan images. In step 508, the processor 606 generates the overlay image 300, 400 and displays the image 300, 400 on a display 608. A radiologist or other user may manipulate, scroll through or otherwise edit any of the original first and second brain scans and overlay images 300, 400 via a user interface 610 which may include any of a keyboard, mouse and/or a touch display on the display 608.

It will be appreciated by those skilled in the art that various modifications and alterations of the invention can be made without departing from the broad scope of the appended claims. Some of these have been discussed above and others will be apparent to those skilled in the art.

The invention claimed is:
1. A method, comprising:
receiving a first data set corresponding to patient data at a first time, the first data set comprising a first brain scan;
receiving a second data set corresponding to patient data at a second time, the second data set comprising a second brain scan;
segmenting a first region of interest in the first data set, wherein the first region of interest is a portion of the first brain scan and comprises a first and a second structure, the second structure being a mirror of the first structure across the sagittal plane;

segmenting a second region of interest in the second data set, wherein the second region of interest is a portion of the second brain scan and comprises the first and second structures, wherein the segmented first and second regions correspond to one another; and aligning the segmented first region of interest with the segmented second region of interest to highlight a first contour indicating a change in size, shape and orientation between the segmented first and segmented second regions of interest, the first contour being the change on the segmented second region of interest.

2. The method of claim 1, further comprising the step of generating an overlay image formed as a composite of the first and second data sets, the overlay image containing the first contour.

3. The method of claim 1, further comprising the step of co-registering the first and second data sets of the overlay.

4. The method of claim 1, wherein the segmentation is one of a bitmask-based segmentation and a model-based segmentation.

5. The method of claim 1, further comprising the step of acquiring the first and second data sets.

6. The method of claim 2, wherein the first contour comprises a first contour line defining a size and shape of the first region and a second contour line defining a size and shape of the second region.

7. The method of claim 6, wherein one or both of a line style and line color of the first contour line is different from a line style and line color of the second contour line.

8. The method of claim 1, further comprising the step of displaying quantitative information relating to one or both of the first region and the second region.

9. The method of claim 8, wherein the quantitative information includes one or more of volume, area, circumference and diameter (taken alone one or both of the short and long axes).

10. The method of claim 8, wherein the quantitative information is automatically displayed with the overlay image.

11. The method of claim 1, wherein the overlay image is generated by a predetermined algorithm.

12. The method of claim 1, wherein the second data set is captured after one of a lapse of a predetermined time period, administration of a treatment and occurrence of a major medical event relative to the first data set.

13. The method of claim 1, wherein the first contour is displayed on one of the first image and the second image.

14. The method of claim 1, further comprising:
receiving a third data set corresponding to patient data at a third time;
segmenting corresponding regions of interest in the first, second and third data sets; and
aligning the corresponding regions of interest with one another to highlight a second contour indicating a change in size, shape and orientation between the first, second and third data sets.

15. A system for diagnosis of a patient, comprising:
a storage unit storing first and second sets of patient data, the first and second data set comprising a first and second brain scan respectively, wherein each of the first and second sets of data is segmented to highlight first and second regions of interest, wherein the first region of interest comprises a first and a second structure of the first brain scan, the second structure being a mirror of the first structure across the sagittal plane and the second region of interest comprises the first and second structures of the second brain scan, the segmented first and second regions corresponding to one another; and
a processor configured to generate an overlay image formed as a composite of the first and second data sets such that the segmented first region of interest is aligned with the segmented second region of interest, the overlay image containing a first contour indicating a change in size, shape and orientation between the first and second regions of interest, the first contour being the change on the segmented second region of interest.

16. The system of claim 15, further comprising a display configured to display the overlay image.

17. The system of claim 15, wherein the processor is configured to display quantitative information relating to one or both of the first region of interest and the second region of interest.

18. The system of claim 15, further comprising a segmentation tool generating segmenting the first and second regions, wherein the segmentation tool uses one of bitmask-based segmentation and model-based segmentation.

19. The system of claim 15, wherein the second data set is captured after one of a lapse of a predetermined time period, administration of a treatment and occurrence of a major medical event relative to the first data set.

20. A non-transitory computer-readable storage medium including a set of instructions executable by a processor, the set of instructions operable to:
generate an overlay image formed as a composite of first and second data sets, wherein the first and second data sets comprise a first and second brain scan respectively, such that the first segmented region of interest of the first data set, the first data set being segmented into a first plurality of corresponding structures, is aligned with a corresponding second segmented region of interest of the second data set, the second data set being segmented into a second plurality of corresponding structures, wherein the first region of interest comprises a first and a second structure of the first brain scan, the second structure being a mirror of the first structure across the sagittal plane and the second region of interest comprises the first and second structures of the second brain scan, the overlay image containing a first contour indicating a change in size, shape and orientation between the segmented first and second regions of interest, the first contour being the change on the segmented second region of interest.

* * * * *